(12) United States Patent
Songer et al.

(10) Patent No.: US 6,458,134 B1
(45) Date of Patent: Oct. 1, 2002

(54) BONE CONNECTOR SYSTEM WITH ANTI-ROTATIONAL FEATURE

(75) Inventors: Matthew N. Songer, Marquette; Greg A. Berrevoets, Skandia; Francis J. Korhonen, Negaunee; Thomas S. Kilpela, Marquette, all of MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 0 days.

(21) Appl. No.: 09/602,771

(22) Filed: Jun. 23, 2000

Related U.S. Application Data

(63) Continuation-in-part of application No. 09/499,881, filed on Feb. 8, 2000, which is a continuation-in-part of application No. 09/375,330, filed on Aug. 17, 1999, now abandoned.

(51) Int. Cl.[7] .............................................. A61B 17/84
(52) U.S. Cl. .......................................... 606/73; 606/53
(58) Field of Search .............................. 606/53, 60, 65, 606/66, 72, 73

(56) References Cited

U.S. PATENT DOCUMENTS

| | | | | |
|---|---|---|---|---|
| 184,718 A | | 11/1876 | Lewis ........................ 403/184 |
| 1,897,196 A | | 2/1933 | Hunt .......................... 411/389 |
| 3,103,926 A | | 9/1963 | Cochran et al. .............. 606/73 |
| 4,716,893 A | * | 1/1988 | Fischer et al. ................ 128/92 |
| 5,334,184 A | * | 8/1994 | Bimman ....................... 606/63 |
| 5,417,692 A | | 5/1995 | Goble et al. .................. 606/73 |
| 5,513,989 A | * | 5/1996 | Crisio ......................... 433/176 |
| 5,522,817 A | * | 6/1996 | Sander et al. ................. 606/72 |
| 5,564,921 A | * | 10/1996 | Marlin ........................ 433/172 |
| 5,667,510 A | * | 9/1997 | Combs ......................... 606/86 |
| 5,827,285 A | * | 10/1998 | Bramlet ....................... 606/60 |
| 5,954,723 A | * | 9/1999 | Spetzler ....................... 606/72 |
| 6,187,008 B1 | * | 2/2001 | Hamman ..................... 606/72 |

* cited by examiner

Primary Examiner—Nicholas D. Lucchesi
Assistant Examiner—Michael B. Priddy
(74) Attorney, Agent, or Firm—Fitch, Even, Tabin & Flannery

(57) ABSTRACT

A bone connector system comprises first and second connector members. At least one, and preferably both, of the connector members carries an external bone screw thread to permit securance within a bone. One of the connector members defines a boss having an outer end with intersecting slots therein to form flexible fingers, the boss having flanges which may be formed by an external screw thread adjacent to the outer end and an external hexagonal engagement surface spaced from the outer end. The other of the connector members defines a bore having grooves which may be formed by an internal screw thread proportioned to engage the flanges on the boss, and a hexagonal engagement portion proportioned to mateably receive and engage the hexagonal engagement surface, when the connectors are brought together. Either or both of the connector members may define guidewire lumens.

22 Claims, 2 Drawing Sheets

BONE CONNECTOR SYSTEM WITH ANTI-ROTATIONAL FEATURE

CROSS REFERENCE TO RELATED APPLICATIONS

This application is a continuation-on-part of copending U.S. application Ser. No. 09/499,881, filed Feb. 8, 2000, entitled "Bone Connector System," which is in turn a continuation-in-part of U.S. application Ser. No. 09/375,330, filed Aug. 17, 1999, entitled "Bone Connector System," now abandoned the disclosures of which are incorporated herein by reference.

BACKGROUND OF THE INVENTION

That application discloses a bone fixation and fusion system, for example for the fusing together of toe bones or the like, by firmly locking them in abutting relation to permit good healing. This is accomplished through the use of male and female connectors, each of which, when bone fission or fixation is the desired result, has external bone threads so that each of the connectors may be driven into a separate piece of bone or opposing ends of the same bone, as at a fracture.

The male connector is a solid body having a slotted boss with external threads adjacent to a distal end. The female connector defines an internally threaded bore in which the boss of the male connector may be threadedly engaged in a somewhat resilient, spring-like manner resulting from the cross cut slots, for retention of the two connectors together.

This threaded interconnection permits the connectors to be engaged in a well-fitting, solid connection which nevertheless is highly adjustable in its length by adjusting the depth to which one connector is inserted into the other. However, the threaded interconnection may also permit one connector to rotate with respect to the other after installation, which may be undesirable or harmful. Previous art does not control rotation.

SUMMARY OF THE INVENTION

By this invention, a bone connector system is provided which comprises first and second connector members. At least one of the connector members carries an external bone screw thread to permit securance within a bone. In the circumstance where two bones or two parts of a bone are being connected together for fusing or the like, both of the connectors may carry external bone screw threads, to permit their separate securance within separate bone parts. Otherwise, one of the connector members may connect to an artificial tooth or another attachment to a bone.

One of the connector members defines a projection or boss having a distal or outer end. Longitudinal slots extend through portions of the boss adjacent to the outer end. The boss also carries a plurality of loops or convolutions of an external screw thread adjacent to the outer end.

The other of the connector members defines a bore for receiving the boss, and having a plurality of loops or convolutions of an internal screw thread which is proportioned to engage the external thread of the boss when the connectors are brought together. The internal screw thread and the external screw thread may fit together with a multiple loop, close, tight fit without any mispositioning. The outer surface of the boss has a portion of non-circular peripheral shape disposed formating engagement in a portion of the bore having a similar non-circular peripheral shape when the boss is disposed in the bone, to prevent relative rotation of the connector members.

If desired, one or both connector members may define a central lumen, to permit a guidewire to extend through either or both connector members to facilitate placement thereof at a desired position in a bone.

DESCRIPTION OF SPECIFIC EMBODIMENTS

Figure 1:
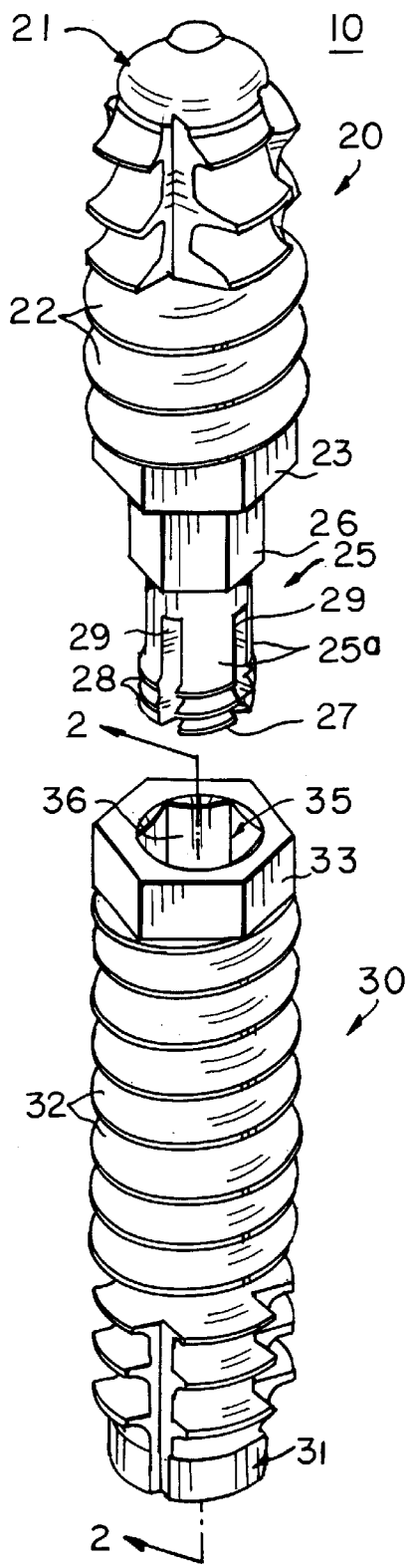
FIG. 1 is a perspective view showing the two separate connector members of the bone connector system of the invention.
Figure 2:
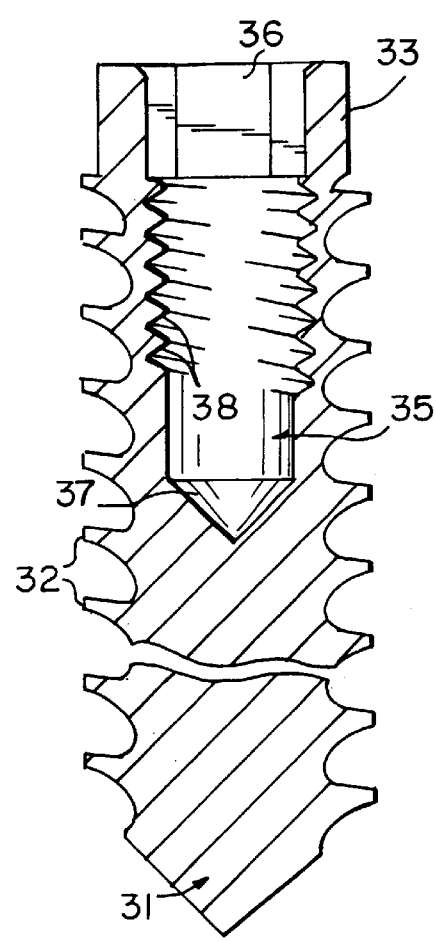
FIG. 2 is an enlarged sectional view, taken generally along line 2—2 of FIG. 1, of one of the connector members.
Figure 3:
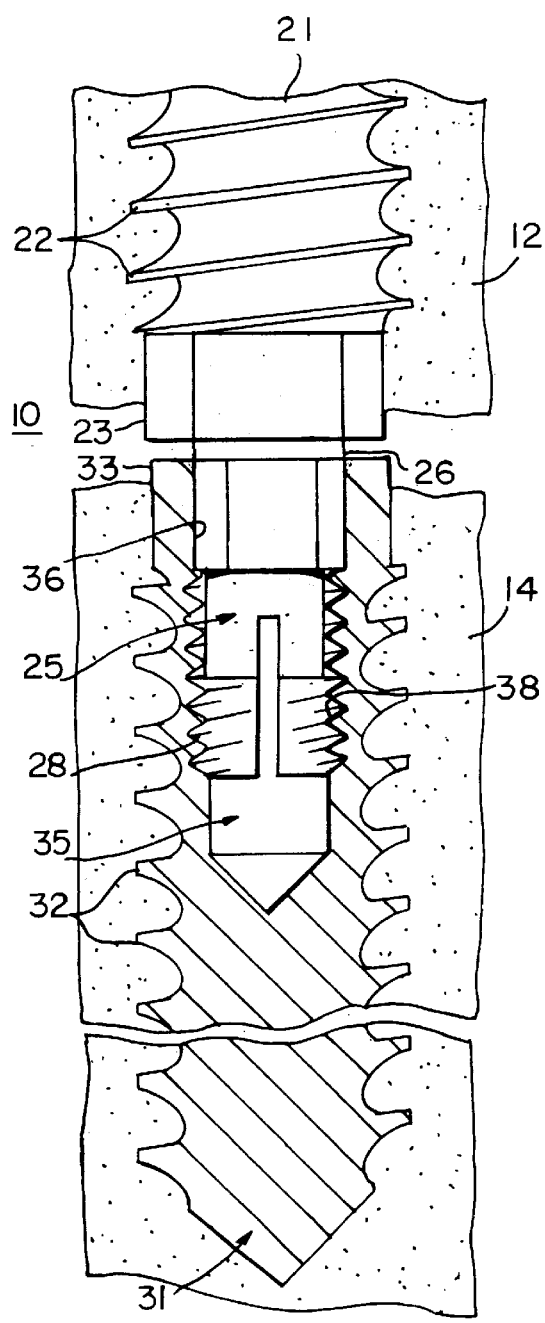
FIG. 3 is an enlarged, fragmentary view in partial longitudinal section of the bone connector system of FIG. 1, shown in a position of implantation within and connecting two bones.

Referring to FIGS. 1–3, bone connector system 10 is shown in FIG. 3 to be implanted between a pair of bones or parts of a bone 12, 14, for example, two bone parts in a toe which need fusion, and are so fused by the installation of the bone connector of system 10.

The bone connector system 10 includes two bone connector members 20 and 30, each of which may be made of a desirable surgically implantable metal. The connector member 20 has an elongated body 21 provided with an external bone screw thread 22 so that the connector member 20 can be fixed in an associated bone or bone part. The connector member 20 also has an external polygonal drive surface 23, which may be hexagonal in shape, to receive an associated wrenching tool or the like to facilitate implanting the connector member 20 in the associated bone or bone part, in a known manner.

The connector member 20 also defines a projecting boss 25 which has an external peripheral engagement surface 26 which is non-circular in shape. The surface 26 may have a polygonal shape, such as hexagonal. The boss 25 has an outer or distal end 27 and is provided with an external thread 28 adjacent to the distal end 27, the loops or convolutions of the thread 28 forming laterally outwardly projecting flanges. Formed in the boss 25 adjacent the distal end 27 are a plurality of slots 29. The slots 29 may be equiangularly spaced around the periphery of the boss 25, with the slots communicating with one another internally of the boss 25, so that the slots 29 cooperate to divide the boss 25 into a plurality of fingers 25a.

The connector member 30 has an elongated body 31 and is provided with an external bone screw thread 32 so that it can be fixed in an associated bone or bone part. The connector member 30 has an external peripheral drive surface 33, which may be polygonal in shape, such as hexagonal, to receive an associated wrenching tool and the like to facilitate implanting the connector member 30 in an associated bone or bone part. Formed in the connector member 30 is a bore 35 which could extend entirely or part-way through the connector member 30. The bore 35 is provided adjacent to an outer end with a peripheral engagement portion 36 which is non-circular in shape, being shaped and dimensioned for mating engagement with the engagement surface 26 of the connector member 20. More specifically, the engagement portion 36 may be polygonal, such as hexagonal. The bore 35 is provided, inboard of the engagement portion 36, with an internal screw thread 38, having plural loops or convolutions which define grooves which form another engagement portion. The screw thread 38 is designed for threaded engagement with the screw thread 28 of the connector member 20.

In use, if two bones or two parts of a bone 12, 14 are to be fused together, the connector members 20 and 30 are, respectively, screwed into the bones or bone parts in a known manner to fixed positions illustrated in FIG. 3. Then, the connector members 20 and 30 are secured together by inserting the boss 25 into the bore 35. This insertion may be accomplished without relative rotation of the parts, because the fingers 25a of the boss 25 have radial flexibility sufficient to permit them to be deflected inwardly so that the loops or convolutions of the external screw thread 28 on the boss 25 can be snapped past the loops or convolutions of the internal screw thread 38 in the bore 35. The boss 25 inserted in the bore 35 until the hexagonal engagement surface 26 enters the hexagonal engagement portion 36 of the bore 35. In this regard, it will be appreciated that, when the connector members 20 and 30 are respectively inserted in the bones 12 and 14, they will be rotated to positions wherein the engagement surface 26 and the engagement portion 36 align with each other. It will also be appreciated that the boss 25 may be inserted into the bore 35 to a variety of different depths, limited by the axial extent of the hexagonal engagement portion 36 of the bore 35, so that the overall length of the bone connector system 10 may be finely adjustable.

Once the engagement surface 26 is mateably engaged with the engagement portion 36, the connector members 20 and 30 are non-rotatable relative to each other.

While the invention has been described with respect to fusing of toe bones or bone parts, it will be appreciated that the bones 12 and 14 may be other types of bones, such as finger bones, adjacent vertebrae or any other adjacent bones which need to be fused together. If only one of the connector members 20 and 30 is mounted in a bone, it will be appreciated that in joining the other connector member to it, the other connector member may initially be rotated to screw the parts together until the engagement surface 26 is about to enter the engagement portion 36, whereupon continued joinder is accomplished by an axial movement.

While the flanges on the boss 25 and the grooves in the bore 35 are respectively formed by helical threads 28 and 38, they could be discrete, annular flanges and grooves, but threads are less expensive to form.

Figure 4:
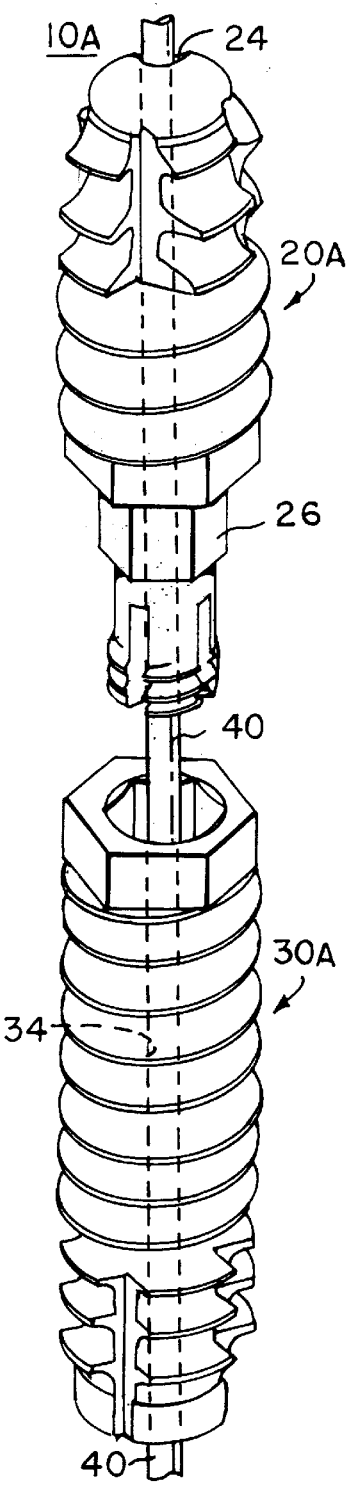
FIG. 4 is a perspective view similar to FIG. 1 of a modified bone connector system.

Referring to FIG. 4, an alternative design of the bone connector system 10A is illustrated, including connector members 20A and 30A, which are respectively substantially the same as the connector members 20 and 30, described above, except that the connector members 20A and 30A respectively define central lumens 24 and 34 extending longitudinally therethrough. This permits the connector members 20A and 30A to be threaded onto a guidewire 40 to facilitate advancement and placement of the respective connector members 20A and 30A into their desired positions.

The matter set forth in the foregoing description and accompanying drawings is offered by way of illustration only and not as a limitation. The actual scope of the protection sought is intended to be defined in the following claims, when viewed in their proper perspective based on the prior art.

We claim:
1. A bone connector system comprising:
first and second connector members;
at least one of said connector members having an external bone screw thread to permit attachment within a bone;
one of the connector members having a bore therein having an outer end;
the bore having an engagement portion of non-circular peripheral shape adjacent to the outer end;
the other of the connector members having a boss dimensioned to be received in the bore;
the boss having an outer engagement surface of non-circular peripheral shape disposed for mating engagement with the first engagement portion when the boss is received in the bore; and
coupling structure interconnecting the first and second members to inhibit removal of the boss from the bore, wherein the coupling structure includes a first portion on the one member and a second portion on the other member, the first portion includes internal peripheral grooves in the bore inboard of the engagement portion, the second portion including external peripheral flanges on the boss adjacent to the distal end thereof and disposed for engagement in the grooves when the boss is received in the bore, and the grooves are formed by an internal helical thread and the flanges are formed by an external helical thread.

2. A bone connector system comprising:
first and second connector members;
at least one of said connector members having an external bone screw thread to permit attachment within a bone;
one of the connector members having a bore therein having an outer end;
the bore having a first engagement portion of non-circular peripheral shape adjacent to the outer end;
the bore having a second engagement portion with internal peripheral grooves disposed inboard of the first engagement portion;
the other of the connector members having a boss dimensioned to be received in the bore;
the boss having a distal end with a slot extending transversely through the boss at the distal end;
the boss having an outer engagement surface of non-circular peripheral shape disposed for mating engagement with the first engagement portion when the boss is received in the bore; and
the boss having external peripheral flanges adjacent to the distal end disposed for engagement in the grooves when the boss is received in the bore, wherein the grooves are formed by an internal helical thread and the flanges are formed by an external helical thread.

3. A bone connector system comprising:
first and second connector members;
at least one of said connector members having an external bone screw thread to permit attachment within a bone;
one of the connector members having a bore therein having an outer end;
the bore having a first engagement portion of non-circular peripheral shape adjacent to the outer end;
the bore having a second engagement portion with internal peripheral grooves disposed inboard of the first engagement portion;
the other of the connector members having a boss dimensioned to be received in the bore;
the boss having a distal end with a slot extending transversely through the boss at the distal end;
the boss having an outer engagement surface of non-circular peripheral shape disposed for mating engagement with the first engagement portion when the boss is received in the bore; and the boss having external peripheral flanges adjacent to the distal end disposed for engagement in the grooves when the boss is received in the bore, wherein the grooves are greater in number than the flanges.

4. A bone connector system comprising:

first and second connector members;

at least one of said connector members having an external bone screw thread to permit attachment within a bone;

one of the connector members having a bore therein having an outer end;

the bore having a first engagement portion of non-circular peripheral shape adjacent to the outer end;

the bore having a second engagement portion with internal peripheral grooves disposed inboard of the first engagement portion;

the other of the connector members having a boss dimensioned to be received in the bore;

the boss having a distal end with a slot extending transversely through the boss at the distal end;

the boss having an outer engagement surface of non-circular peripheral shape disposed for mating engagement with the first engagement portion when the boss is received in the bore; and the boss having external peripheral flanges adjacent to the distal end disposed for engagement in the grooves when the boss is received in the bore, wherein at least one of the connector members has a lumen extending therethrough.

5. The system of claim 4, wherein both of the connector members have lumens extending therethrough.

6. A bone connector system comprising:

first and second connector members;

at least one of said connector members having an external bone screw thread to permit attachment within a bone;

one of the connector members having a bore therein having an outer end, the bore having an engagement portion of non-circular peripheral shape adjacent to the outer end, the other of the connector members having a boss dimensioned to be received in the bore; and the boss having an outer engagement surface of non-circular peripheral shape disposed for mating engagement with the first engagement portion when the boss is received in the bore, wherein at least one of the connector members has a lumen extending therethrough.

7. The system of claim 6, wherein both of the connector members have lumens extending therethrough.

8. A bone connector system for approximating bone surfaces of small bone portions in substantially fixed position relative to each other, the bone connector system comprising:

female and male connector members each having an axis and a predetermined length therealong sized for being implanted in the small bone portions;

external bone screw threads along the length of the connector members to allow the connector members to be implanted in the respective bone portions including the bone surfaces to be approximated;

an axial bore of the female connector member having an open end thereof;

an attachment portion of the male connector member sized to be received in the axial bore and extending for a predetermined portion length along the length of the male connector member;

at least one radial projection and at least one recess wherein the projection is associated with one of the male connector member attachment portion and the female connector member bore and the recess is associated with the other of the male connector member and female connector member bore to provide a snap-fit attachment between the implanted connector members for keeping the bone surfaces approximated;

cooperating engagement surfaces in the female connector member bore and on the male connector member attachment portion, each extending axially for a predetermined surface length along the respective lengths of the connector members and having other than circular configurations; and predetermined positions of the engagement surface and the radial projection or recess along the attachment portion of the male connector member so that with the projection received in the recess to snap-fit the connector members together, the engagement surfaces will be in overlapping relation for a predetermined overlap distance along the predetermined axial surface lengths thereof sufficient to inhibit relative rotation between the implanted connector members.

9. The bone connector system of claim 8 wherein the attachment portion includes a generally cylindrical wall and the at least one radial projection and at least one recess comprise external threads on the cylindrical wall and internal threads in the female connector bore; and a predetermined axial spacing between the predetermined positions of the external threads and the male connector engagement surface of sufficient length to allow the external threads to resiliently cam past the internal threads with axial insertion of the attachment portion into the bore to be non-rotatably received therein.

10. The bone connector system of claim 9 wherein the cylindrical wall includes an axial slot in the wall that extends along the axial spacing for increasing flexibility of the wall for snap-fitting of the threads to each other and keeping wall length to a minimum.

11. The bone connector system of claim 8 wherein the at least one radial projection and at least one recess comprise a plurality of annular projections and a plurality of annular grooves, and the attachment portion has a split construction along the projections to provide sufficient resiliency to the attachment portion for camming the projections into mating engagement with the grooves with axial insertion of the attachment portion into the bore.

12. The bone connector system of claim 11 wherein the projections and grooves comprise external and internal helical threads, respectively.

13. The bone connector system of claim 8 wherein the connector members include stop surfaces extending transverse to the respective axes thereof and positioned relative to each other so that with the stop surfaces in abutting relation, the predetermined overlap distance corresponds to the predetermined surface length of the engagement surface in the female connector member bore to maximize resistance to relative rotation between the connector members.

14. The bone connector system of claim 13 wherein the connector members each have a drive head including drive surfaces and the transverse stop surfaces with the drive head of the male connector member being larger than the drive head of female connector member so that the stop surface on the male connector member drive head abuts the stop surface on the female connector drive head.

15. The bone connector system of claim 8 wherein the configurations of the engagement surfaces are polygonal, and the female connector member has a drive head adjacent the open end of the bore and including an external polygonal drive surface for turning of the female connector member about the axis thereof for threading into a bone portion with the female connector polygonal engagement surface being an internal surface of the drive head.

16. The bone connector system of claim 15 wherein the polygonal engagement surfaces each comprise hex surfaces sized for a close mating fit therebetween.

17. The bone connector system of claim 8 wherein the attachment portion has a stepped configuration to provide a larger and smaller sections thereof and a transverse shoulder surface therebetween with the predetermined position of the engagement surface being on the larger section and the predetermined position of the radial projection or recess being on the smaller section.

18. The bone connector system of claim 17 wherein the male connector member has a drive head adjacent the attachment portion larger section and enlarged in a radial direction relative thereto to form another transverse shoulder surface disposed between the enlarged drive head and the attachment portion.

19. The bone connector system of claim 18 wherein the at least one radial projection and the at least one recess comprise external threads on the attachment portion and internal threads in the bore including a thread closest to the bore opening positioned to engage the shoulder surface between the attachment portion sections to stop axial insertion of the attachment portion into the bore with the threads snap-fit together.

20. The bone connector system of claim 19 wherein the transverse shoulder surface between the drive head and attachment portion is positioned to abut the female connector member about the open end of the bore with the shoulder surface between the attachment portion sections abutting the stop thread.

21. The bone connector system of claim 8 wherein the at least one radial projection and at least one recess comprise a plurality of projections and recesses on the male connector member and in the female connector member bore, respectively, and the predetermined positions allow the connector members to be non-rotatably snap-fit together at a plurality of different axial positions with respect to each other via the plurality of projections and recesses.

22. The bone connector system of claim 11 wherein the overlap distance between the engagement surfaces increases as the connector members are snap-fit together at successive ones of the different axial positions.

* * * * *

UNITED STATES PATENT AND TRADEMARK OFFICE
CERTIFICATE OF CORRECTION

PATENT NO.    : 6,458,134 B1
DATED         : October 1, 2002
INVENTOR(S)   : Songer et al.

It is certified that error appears in the above-identified patent and that said Letters Patent is hereby corrected as shown below:

Column 8,
Line 21, change "11" to -- 21 --.

Signed and Sealed this

Twentieth Day of May, 2003

JAMES E. ROGAN
*Director of the United States Patent and Trademark Office*